US009572947B2

(12) United States Patent
Grashow et al.

(10) Patent No.: US 9,572,947 B2
(45) Date of Patent: Feb. 21, 2017

(54) PATIENT INTERFACE DEVICE WITH NOSE BRIDGE ADJUSTMENT

(71) Applicant: KONINKLIJKE PHILIPS N.V., Eindhoven (NL)

(72) Inventors: Jonathan Sayer Grashow, Cheswick, PA (US); Lauren Patricia Chodkowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 251 days.

(21) Appl. No.: 14/357,851

(22) PCT Filed: Oct. 31, 2012

(86) PCT No.: PCT/IB2012/056062
§ 371 (c)(1),
(2) Date: May 13, 2014

(87) PCT Pub. No.: WO2013/072799
PCT Pub. Date: May 23, 2013

(65) Prior Publication Data
US 2014/0290664 A1 Oct. 2, 2014

Related U.S. Application Data (60) Provisional application No. 61/559,829, filed on Nov. 15, 2011.

(51) Int. Cl.
*A61M 16/06* (2006.01)
(52) U.S. Cl.
CPC ......... *A61M 16/0622* (2014.02); *A61M 16/06* (2013.01); *A61M 16/0633* (2014.02);
(Continued)
(58) Field of Classification Search
CPC .............. A61M 16/06; A61M 16/0622; A61M 16/0683;A61M 16/0633; A61M 16/0644; A61M 16/0605; A61M 16/065; A61M 16/0661; A61H 9/005; A61H 2201/01; A62B 18/00; A62B 18/025
See application file for complete search history.

(56) References Cited

U.S. PATENT DOCUMENTS 3,513,841 A * 5/1970 Seeler .................. A62B 18/084
128/201.23
5,904,145 A * 5/1999 Reid ...................... A61F 13/069
128/898
(Continued)

FOREIGN PATENT DOCUMENTS

| CN | 1972727 A | 5/2007 |
| CN | 102085407 A | 6/2011 |

(Continued)

*Primary Examiner* — Tan-Uyen (Jackie) T Ho
*Assistant Examiner* — Margaret Luarca
(74) *Attorney, Agent, or Firm* — Michael W. Haas (57) ABSTRACT

A patient interface device includes a bladder assembly having a headgear bladder member, a nose bridge bladder member, and a connecting tube member provided between the headgear bladder member and the nose bridge bladder member. The headgear bladder member is in sealed fluid communication with the nose bridge bladder member through the connecting tube member, and is filled with a fluid medium. The bladder assembly is structured such that the nose bridge bladder member will be inflated as a pressure on the headgear bladder member increases and such that the nose bridge bladder member will be deflated as the pressure on headgear bladder member decreases. Inflation of the nose bridge bladder member causes the top of a cushion member to move toward the patient's nose bridge, and deflation of the nose bridge bladder member causes the top of the cushion member to move away from the patient's nose bridge.

25 Claims, 8 Drawing Sheets

(52) U.S. Cl.
CPC .... *A61M 16/0638* (2014.02); *A61M 16/0644* (2014.02); *A61M 16/0683* (2013.01)

(56) References Cited

U.S. PATENT DOCUMENTS

| | | |
|---|---|---|
| 2004/0211428 A1 | 10/2004 | Jones, Jr. |
| 2004/0216747 A1 | 11/2004 | Jones, Jr. |
| 2006/0118117 A1* | 6/2006 | Berthon-Jones ...... A61M 16/06 128/206.21 |
| 2007/0107733 A1* | 5/2007 | Ho ........................ A61M 16/06 128/206.24 |
| 2007/0163594 A1* | 7/2007 | Ho .................... A61M 16/0633 128/206.24 |
| 2010/0024811 A1 | 2/2010 | Henry |
| 2010/0163049 A1 | 7/2010 | Osier |
| 2011/0126838 A1 | 6/2011 | Alberici |

FOREIGN PATENT DOCUMENTS

| | | |
|---|---|---|
| EP | 2005985 A2 | 12/2008 |
| WO | WO2005123166 A1 | 12/2005 |
| WO | WO2006000046 A1 | 1/2006 |
| WO | WO2009062265 A1 | 5/2009 |

* cited by examiner

PATIENT INTERFACE DEVICE WITH NOSE BRIDGE ADJUSTMENT

CROSS-REFERENCE TO RELATED APPLICATIONS

This patents application claims the priority benefit under 35 U.S.C §371 of international patent application no. PCT/IB2012/056062, filed Oct. 31, 2012, which claims the priority benefit under 35 U.S.C. §119(e) of U.S. Provisional Application No. 61/559,829 filed on Nov. 15, 2011, the contents of which are herein incorporated by reference.

BACKGROUND OF THE INVENTION

1. Field of the Invention

The present invention relates to patient interface devices for communicating a flow of gas with an airway of a user, and, in particular, to a patient interface device including a bladder assembly structured to provide automatic adjustment of nose bridge pressure.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. The patient interface device interfaces the ventilator or pressure support device with the airway of the patient, so that a flow of breathing gas can be delivered from the pressure/flow generating device to the airway of the patient.

Typical designs for the mask component of a patient interface device include a faceplate having a cushion attached thereto which seals around the nose and sometimes the mouth of the patient. The faceplate is often connected to a forehead support having a forehead pad which provides an additional point to anchor the mask on the face of the patient. The faceplate and/or faceplate/forehead support arrangement is typically strapped to the head of the patient using a headgear component comprised of upper straps connected to the faceplate or forehead support and lower straps connected to the faceplate. The upper straps are typically tightened or loosened to adjust the fit of the upper portion of the cushion with respect to the patient's face (particularly around the nose bridge). The lower straps are typically tightened or loosened to adjust the fit of the remainder of the cushion (especially the lower portion) with respect to the patient's face.

Because such patient interface devices are typically worn for an extended period of time, it is important for the headgear component to maintain the mask component of the device in a tight enough seal against the patient's face without causing discomfort. As mentioned above, the upper straps are typically tightened in order to move the upper portion of the mask cushion into the nose bridge. If significant adjustment is required, this may require severe tightening of the upper headgear straps. In prior art designs, this strategy, while producing the desired effect of improving the cushion fit around the nose bridge, also produces the unwanted side effect of generating uncomfortable pressure on portions of the patients head, such as the patient's forehead (possibly resulting in red mark formation on the skin).

SUMMARY OF THE INVENTION

Accordingly, it is an object of the present invention to provide a patient interface device that overcomes the shortcomings of conventional patient interface device. This object is achieved according to one embodiment of the present invention by providing a patient interface device that includes a fluid filled bladder assembly in a configuration where the bladder assembly functions as a mechanism for automatically adjusting a fit of the patient interface device at the nose bridge of the patient.

It is yet another object of the present invention to provide a method of adjusting a patient interface device that does not suffer from the disadvantages associated with conventional adjustment techniques. This object is achieved by providing a method that includes adjusting the nose bridge position of a cushion of the patient interface device by applying pressure to a headgear bladder member of a bladder assembly provided as part of the patient interface device.

In one embodiment, a patient interface device is provided that includes a patient sealing assembly including a cushion member, a headgear assembly coupled to the patient sealing assembly, the headgear assembly including a strap, and a bladder assembly having a headgear bladder member coupled to the strap, a nose bridge bladder member positioned adjacent a top portion of the cushion, and a connecting tube member provided between the headgear bladder member and the nose bridge bladder member. The headgear bladder member is in sealed fluid communication with the nose bridge bladder member through the connecting tube member, the bladder assembly being filled with a fluid medium, wherein the bladder assembly is structured such that the nose bridge bladder member will be inflated as a pressure on the headgear bladder member increases in response to a force applied thereto by the strap increasing and such that the nose bridge bladder member will be deflated as the pressure on headgear bladder member decreases in response to the force applied thereto by the strap decreasing, and wherein inflation of the nose bridge bladder member causes the top of the cushion member to move in a first direction and deflation of the nose bridge bladder member causes the top of the cushion member to in a second direction opposite the first direction.

In another embodiment, a method of adjusting a patient interface device is provided. The method includes coupling the patient interface device to the patient's head, the patient interface device including a patient sealing assembly having a cushion member, and a bladder assembly having a headgear bladder member, a nose bridge bladder member, and a connecting tube member provided between the headgear bladder member and the nose bridge bladder member, wherein the headgear bladder member is in sealed fluid communication with the nose bridge bladder member through the connecting tube member, the bladder assembly being filled with a fluid medium. The method further includes moving a top of the cushion member toward a nose bridge of the patient by inflating the nose bridge bladder member by increasing a pressure on the headgear bladder member, and moving the top of the cushion member away from the nose bridge of the patient by deflating the nose bridge bladder member by decreasing the pressure on headgear bladder member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
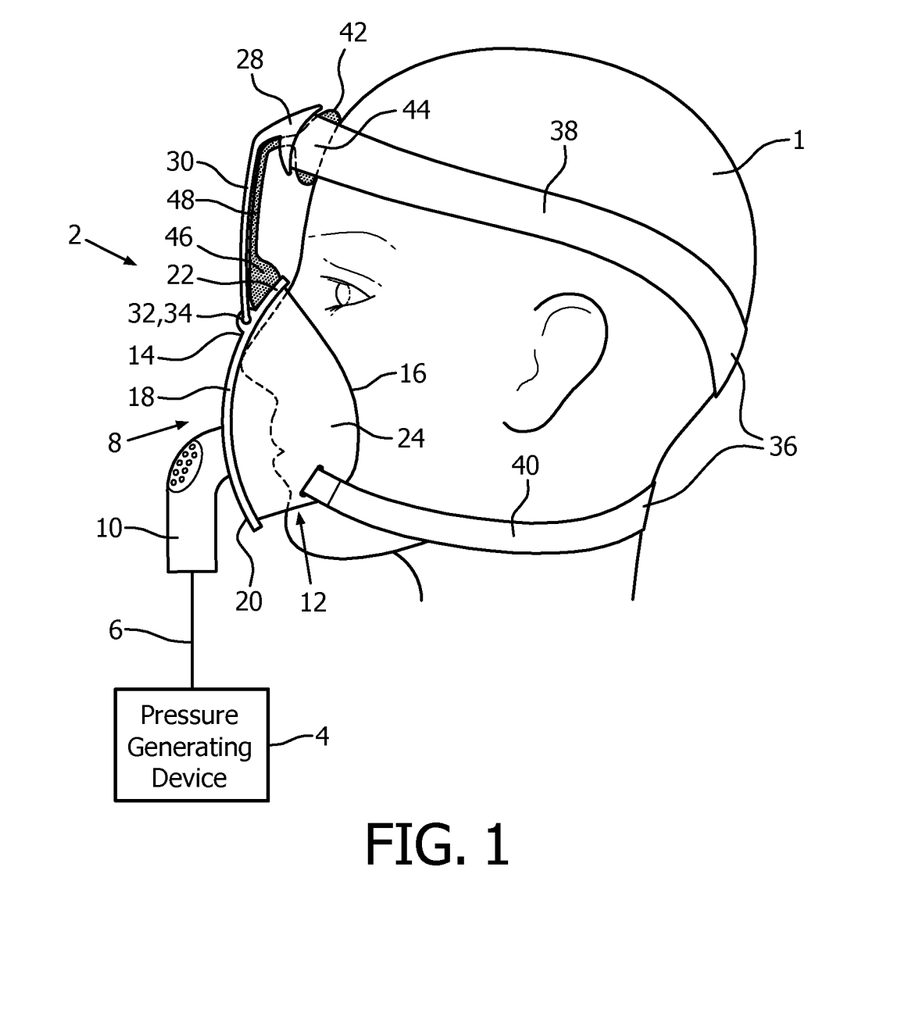
FIG. 1 is a schematic diagram of a system adapted to provide a regimen of respiratory therapy to a patient according to one exemplary embodiment of the present invention.
Figure 2:
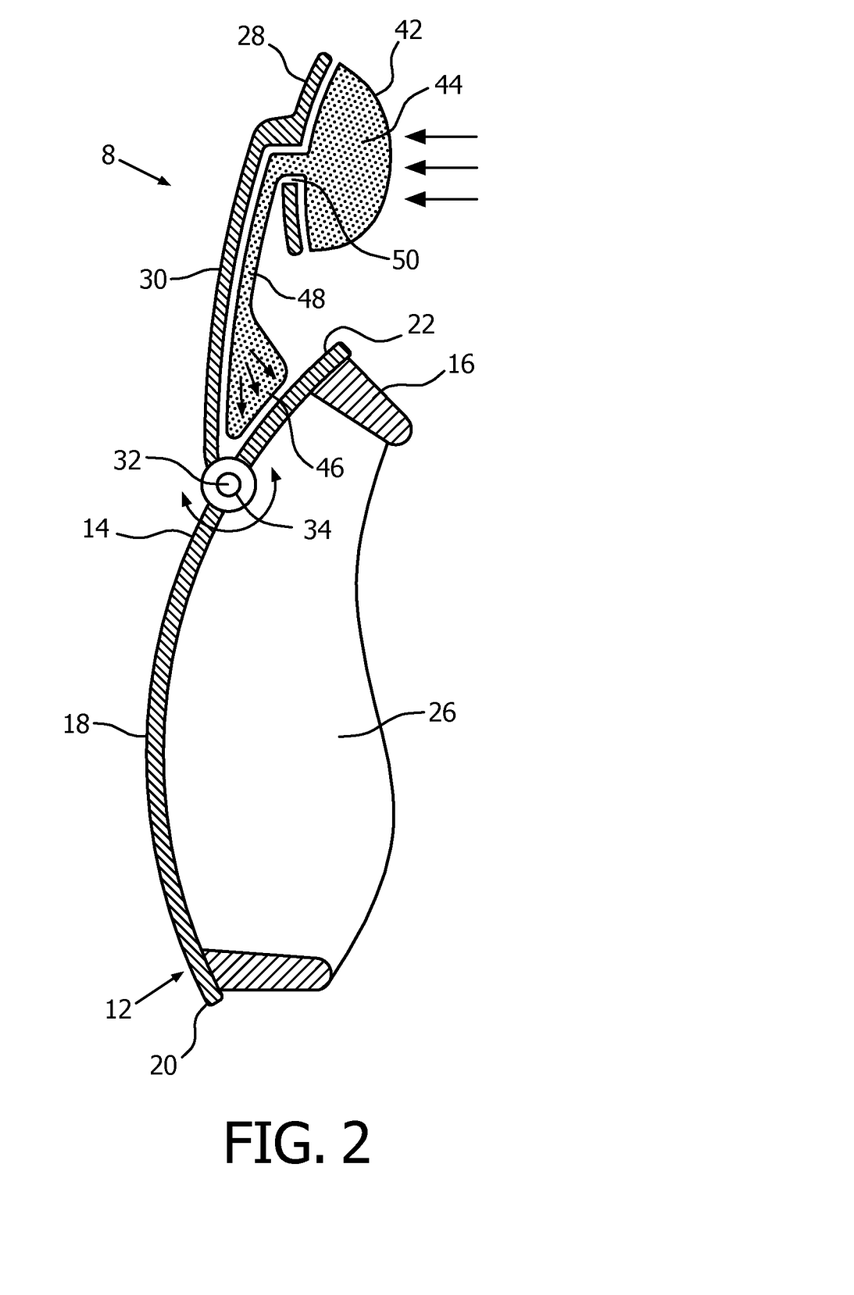
FIG. 2 is a side elevational view in partial cross-section of a patient interface device of the system of FIG. 1 according to an exemplary embodiment.

A system 2 adapted to provide a regimen of respiratory therapy to a patient according to one exemplary embodiment is generally shown in FIG. 1. System 2 includes a pressure generating device 4, a delivery conduit 6, and a patient interface device 8 having a fluid coupling conduit 10. FIG. 2 is a side elevational view in partial cross-section of patient interface device 8 of system 2. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

As seen in FIGS. 1 and 2, in the exemplary embodiment, patient interface 8 includes a patient sealing assembly 12, which in the illustrated embodiment is a nasaVoral mask structured to fit over the nose and mouth of the patient 1. However, other types of patient sealing assemblies, such as, without limitation, a nasal mask or a nasal cushion, which facilitate the delivery of the flow of breathing gas to the airway of a patient, may be substituted for patient sealing assembly 12 while remaining within the scope of the present invention. Patient sealing assembly 12 includes a frame member 14 having a cushion member 16 coupled thereto.

In the illustrated embodiment, frame member 14 is made of a rigid or semi-rigid material, such as, without limitation, an injection molded thermoplastic or silicone, and includes a faceplate portion 18 having a central opening formed therein. As seen in FIG. 1, fluid coupling conduit 10 is coupled to faceplate portion 18 through the opening formed therein, which configuration allows the flow of breathing gas from pressure generating device 4 to be communicated to an interior space defined by cushion member 16, and then to the airway of a patient.

In the illustrated embodiment, cushion member 16 is defined from a unitary piece of soft, flexible, cushiony, elastomeric material, such as, without limitation, silicone, an appropriately soft thermoplastic elastomer, a closed cell foam, or any combination of such materials. Also in the illustrated embodiment, patient sealing assembly 12 has a generally triangular shape including a bottom region 20, an apex region 22 located opposite bottom region 20, a first side region 24 (FIG. 1) and a second side region 26 (FIG. 2) located opposite first side region 24. As a result, both faceplate portion 18 of frame member 14 and cushion member 16 will have associated bottom, apex and first and second side regions (not labeled individually in FIGS. 1 and 2).

In the exemplary embodiment, frame member 14 also includes a forehead support member 28 that is coupled to faceplate portion 18 by a connecting member 30. As described in greater detail elsewhere herein, forehead support member 28 and connecting member 30 are pivotably coupled to faceplate portion 18. More specifically, in the illustrated, exemplary embodiment, a bottom end of connecting member 30 is provided with pin members 32 on opposite sides thereof Pin members 30 are rotatably received within orifices 34 provided on faceplate portion 18 in a manner that permits connecting member 30 to pivot relative to faceplate portion 18 as shown by the arrows in FIG. 2. Other suitable pivoting mechanism, such as a living hinge, may be employed in place of pin member 32 and orifices 34 to provide the pivoting functionality just described.

In addition, patient interface device 8 includes a headgear component 36 for coupling patient interface device 8 to the head of patient 1. Headgear component 36 includes upper straps 38 which are adjustably coupled to forehead support member 28 by a suitable mechanism (such as looped connector elements) and lower straps 40 which are adjustably coupled to cushion member 16 by a suitable mechanism (such as looped connector elements). Alternatively, lower straps 40 may be coupled to the sides of faceplate portion 18.

In the illustrated, exemplary embodiment, patient interface device 8 further includes a bladder assembly 42, which, as described in greater detail herein, provides for automatic nose bridge adjustment. Bladder assembly 42 includes a headgear bladder member 44 that is in sealed fluid communication with a nose bridge bladder member 46 through a connecting tube member 48. In the illustrated embodiment, bladder assembly 42 is a unitary member wherein headgear bladder member 44, nose bridge bladder member 46 and connecting tube member 48 are formed as a unitary structure, for example using a molding technique. Alternatively, headgear bladder member 44, nose bridge bladder member 46 and connecting tube member 48 may be formed as separate components that are joined to one another in a fluid tight manner Bladder assembly 42 is made from a flexible, non-porous material, such as, without limitation, a rubber material, a polymer (e.g., silicone), or a sealed fabric, and is filled with a fluid medium. The fluid medium may be a gas, such as, without limitation, air, a liquid, such as, without limitation, water, a saline solution, or mineral oil, another suitable material that is able to flow, such as a gel, or any combination of such fluids. The fluid medium is free to flow within bladder assembly 42, i.e., back and forth between headgear bladder member 44 and nose bridge bladder member 46 through connecting tube member 48, thereby making bladder assembly 42 a resilient member.

In the exemplary embodiment shown in FIGS. 1 and 2, bladder assembly 42 is positioned under/beneath forehead support member 28 and connecting member 30. In particular, as seen in FIGS. 1 and 2, headgear bladder member 44 is positioned behind forehead support member 28 and is structured to function as a forehead cushion that engages the forehead of patient 1. Connecting tube member 48 is received and extends through an orifice 50 provided in forehead support member 28 and thereafter extends along a back surface of connecting member 30 to nose bridge bladder member 46. As seen in FIGS. 1 and 2, nose bridge bladder member 46 is positioned between the bottom end of connecting member 30 and the apex region of faceplate portion 18 (in engagement therewith) at a point that is adjacent the pivot point defined by pin members 32 and orifices 34 (i.e., adjacent the nose bridge of patient 1). As seen in FIGS. 1 and 2, in this embodiment, bladder assembly 42 is not in fluid communication with cushion member 16.

The effect of the arrangement just described is that, as nose bridge bladder member 46 is inflated/deflated (as a result of fluid movement within bladder assembly 42) according to the pressure applied to headgear bladder member 44 by adjustment of upper straps 38, faceplate portion 18 and cushion member 16 rotate about the pivot point defined by pin members 32 and orifices 34. This rotation causes the apex region of both faceplate portion 18 and cushion member 16 to move with respect to the nose bridge of patient 1, moving closer as the pressure on headgear bladder member 44 increases (i.e., as upper straps 38 are tightened) and moving away as the pressure on headgear bladder member 44 decreases (i.e., as upper straps 38 are loosened). Thus, tightening of straps 38 compresses headgear bladder member 44 and pushes the fluid medium to nose bridge bladder 46 (see arrows in FIG. 2), thereby tightening the fit of cushion member 16 against the nose of patient 1, and loosening of straps 38 decompresses headgear bladder member 44 and pushes the fluid medium away from nose bridge bladder 46, thereby loosening the fit of cushion member 16 against the nose of patient 1.

Figure 3:
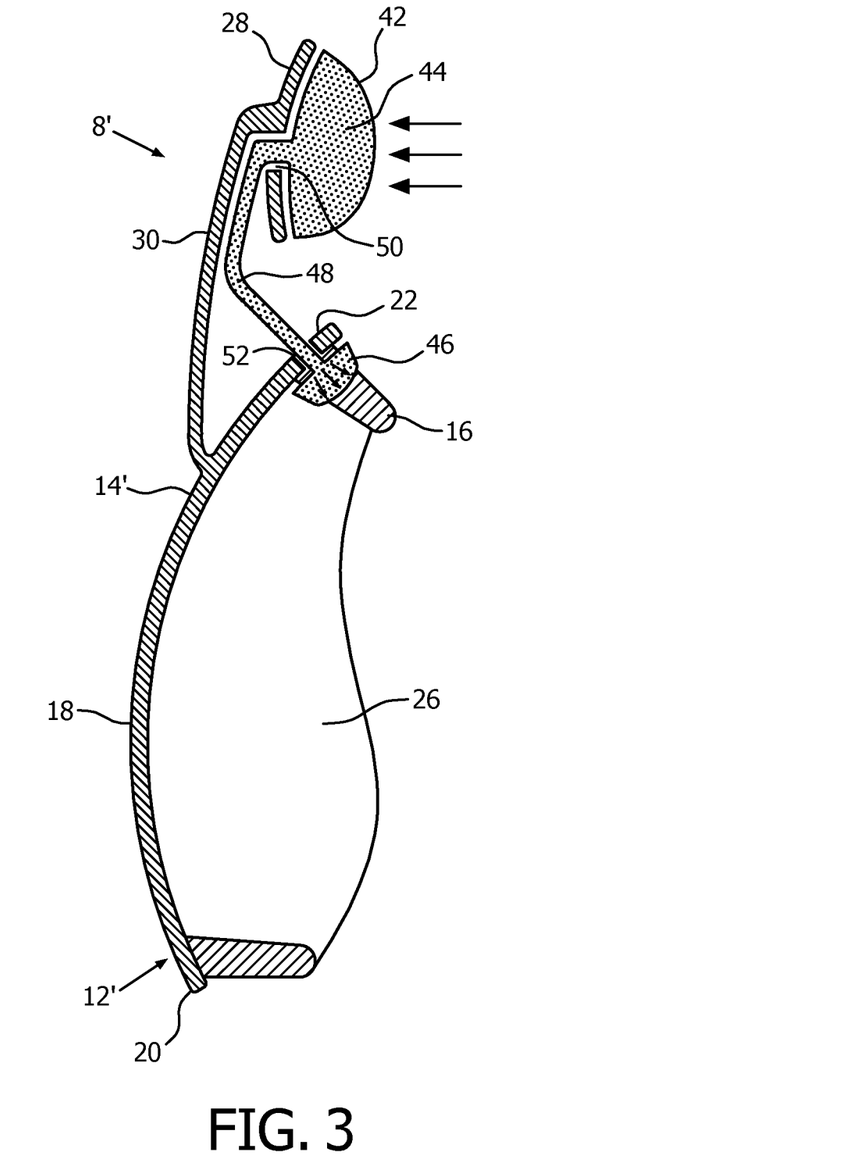
FIG. 3 is a side elevational view in partial cross section of a patient interface device according to an alternative exemplary embodiment of the present invention that may be employed in the system of FIG. 1.

FIG. 3 is a side elevational view in partial cross-section of a patient interface device 8' according to an alternative exemplary embodiment of the present invention. Patient interface device 8' includes a number of the same components as patient interface device 8, and like parts are labeled with like reference numerals. In this embodiment, frame member 14' includes an orifice 52 in apex region 22. As seen in FIG. 3, connecting tube member 48 of bladder assembly 42 is received and extends through orifice 52 such that nose bridge bladder member 46 is mounted between the rear of the apex region of faceplate portion 18 and the apex region of cushion member 16. As nose bridge bladder member 46 is inflated/deflated according to the pressure applied to headgear bladder member 44 by upper straps 38, cushion member 16 itself is translated with respect to the nose bridge of patient 1, moving closer as the pressure on headgear bladder member 44 increases (i.e., as upper straps 38 are tightened) and moving away as the pressure on headgear bladder member 44 decreases (i.e., as upper straps 38 are loosened).

Figure 4:
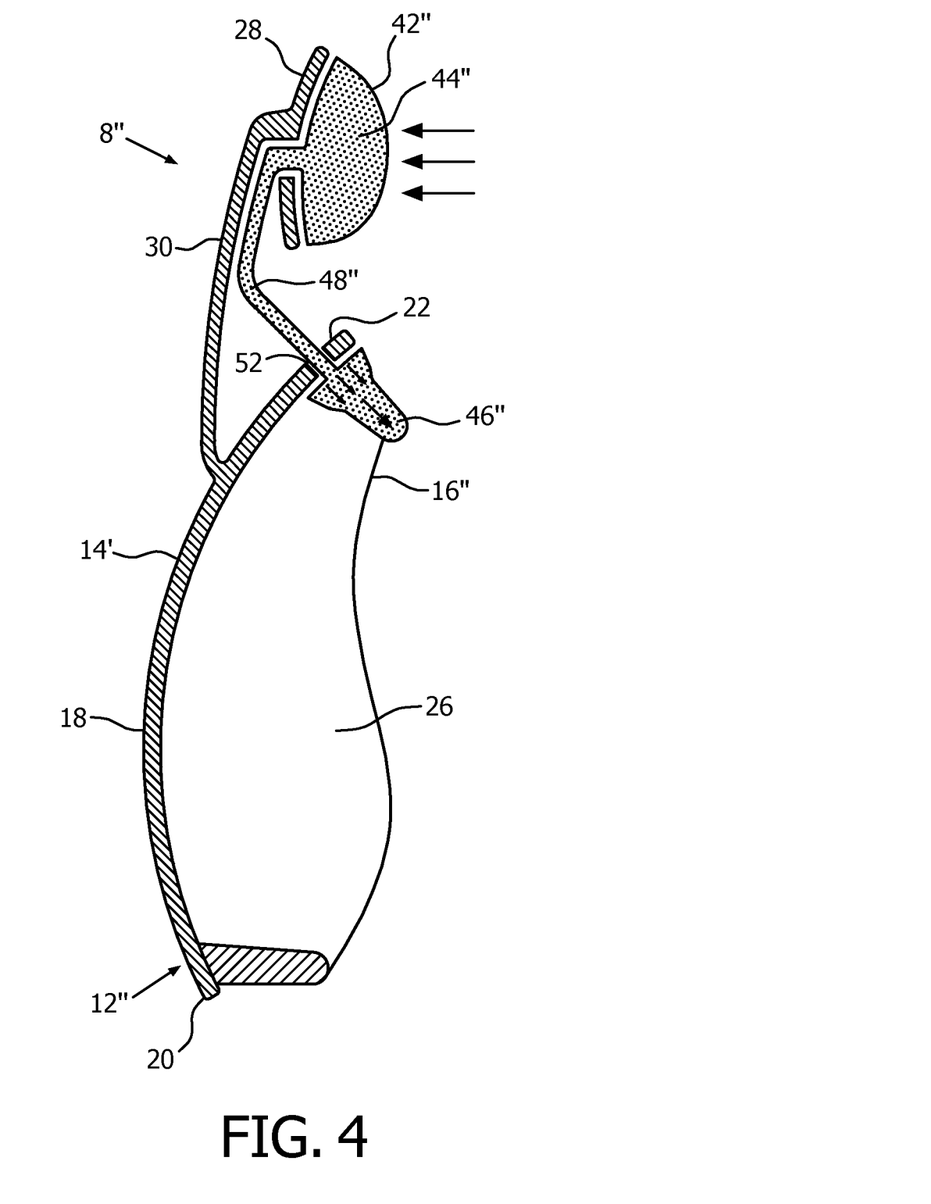
FIG. 4 is a side elevational view in partial cross section of a patient interface device according to another alternative exemplary embodiment of the present invention that may be employed in the system of FIG. 1.

FIG. 4 is a side elevational view in partial cross-section of a patient interface device 8" according to another alternative exemplary embodiment of the present invention. Patient interface device 8" includes a number of the same components as patient interface device 8', and like parts are labeled with like reference numerals. In this embodiment, as in patient interface device 8', frame member 14' includes an orifice 52 in apex region 22. In addition, patient interface device 8" includes an alternative cushion member 16" and an alternative bladder assembly 42". In particular, alternative bladder assembly 42" includes headgear bladder member 44", connecting tube member 48" (which is received and extends through orifice 52), and nose bridge bladder member 46", wherein nose bridge bladder member 46" forms an integral part of the apex region of cushion 16". In this arrangement, nose bridge bladder member 46" is inflated/deflated according to the pressure applied to headgear bladder member 44" as described elsewhere herein, and, as a result, moves toward and away from the nose bridge of patient 1.

Figure 5:
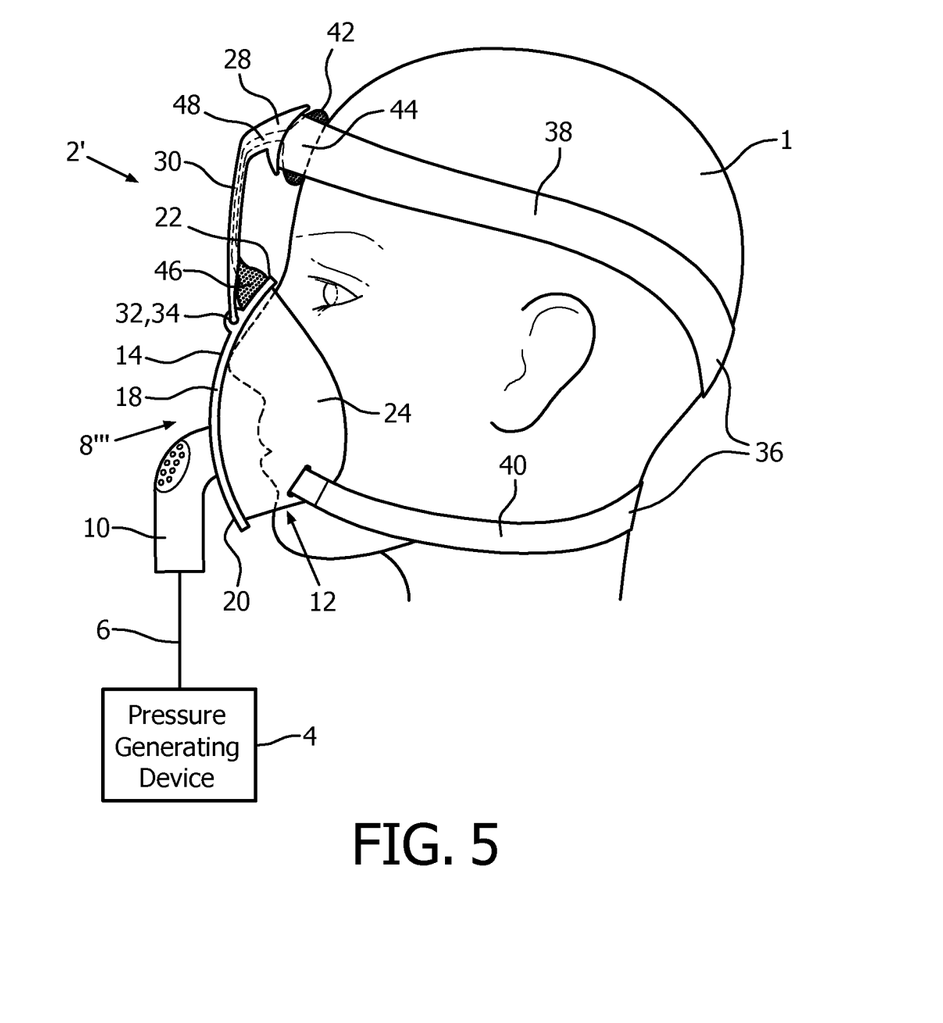
FIGS. 5-8 are schematic diagrams of systems adapted to provide a regimen of respiratory therapy to a patient according to further alternative exemplary embodiments of the present invention.

A system 2' adapted to provide a regimen of respiratory therapy to a patient according to a further exemplary embodiment is generally shown in FIG. 5. System 2' includes a number of the same components as system 2, and like parts are labeled with like reference numerals. In system 2', and in particular in alternative patient interface device 8''' thereof, rather than connecting tube member 48 extending along a back surface of connecting member 30 to nose bridge bladder member 46, connecting tube member 48 extends within a channel provided in connecting member 30 and exits through an orifice provided at the bottom end of connecting member 30 where it meets nose bridge bladder member 46 as seen in FIG. 5. As still a further alternative, connecting tube member 48 can be routed within and/or around other existing parts of patient interface device 8''' as convenient.

Thus, the various exemplary embodiments described above in connection with FIGS. 1-5 provided a patient interface device wherein a fluid filled bladder assembly is provided as part of the patient interface device in a configuration where the bladder assembly functions both as a forehead pad and as a mechanism for automatically adjusting a fit of the patient interface device at the nose bridge of the patient based on/responsive to tightening and loosening of the headgear straps of the patient interface device.

Figure 6:
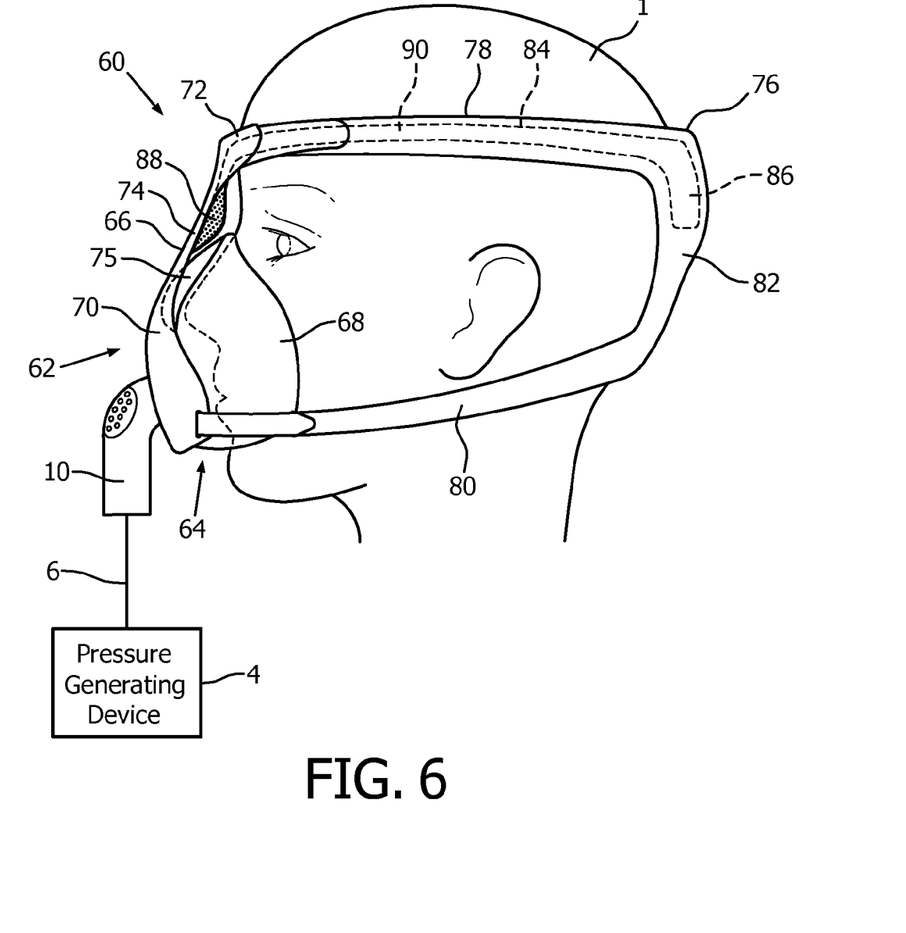

A system 60 adapted to provide a regimen of respiratory therapy to a patient according to a further alternative exemplary embodiment is generally shown in FIG. 6. System 60 includes a pressure generating device 4, a delivery conduit 6, and a fluid coupling conduit 10 as those components are described elsewhere herein. System 60 also includes an alternative patient interface device 62 as described below.

As seen in FIG. 6, patient interface 62 includes a patient sealing assembly 64, which in the illustrated embodiment is a nasal/oral mask structured to fit over the nose and mouth of the patient 1. However, other types of patient sealing assemblies, such as, without limitation, a nasal mask or a nasal cushion, which facilitate the delivery of the flow of breathing gas to the airway of a patient, may be substituted for patient sealing assembly 64 while remaining within the scope of the present invention. Patient sealing assembly 64 includes a frame member 66 having a cushion member 68 coupled thereto.

In the illustrated embodiment, frame member 66 is made of a rigid or semi-rigid material, such as, without limitation, an injection molded thermoplastic or silicone, and includes a faceplate portion 70 having a central opening formed therein. As seen in FIG. 6, fluid coupling conduit 10 is coupled to faceplate portion 70 through the opening formed therein, which configuration allows the flow of breathing gas from pressure generating device 4 to be communicated to an interior space defined by cushion member 68, and then to the airway of a patient.

In the illustrated embodiment, cushion member 68 is defined from a unitary piece of soft, flexible, cushiony, elastomeric material, such as, without limitation, silicone, an appropriately soft thermoplastic elastomer, a closed cell foam, or any combination of such materials. Also in the illustrated embodiment, patient sealing assembly 64 has a generally triangular shape similar to patient sealing assembly 12 described elsewhere herein.

In the illustrated embodiment, frame member 66 also includes a forehead support member 72 that is coupled to faceplate portion 70 by a connecting member 74. Forehead support member 66 and connecting member 74 are pivotably coupled to faceplate portion 70.

In addition, patient interface device 64 includes a headgear component 76 for coupling patient interface device 64 to the head of patient 1. Headgear component 76 includes upper straps 78 which are adjustably coupled to forehead support member 72 by a suitable mechanism (such as looped connector elements) and lower straps 80 which are adjustably coupled to the sides of faceplate portion 70 by a suitable mechanism (such as looped connector elements). Headgear component 76 further includes a rear portion 82 to which the upper straps 78 and the lower straps 80 are coupled.

In the illustrated, exemplary embodiment, patient interface device 64 further includes a bladder assembly 84, which, as described in greater detail herein, provides for automatic nose bridge adjustment. Bladder assembly 84 includes a headgear bladder member 86 that is in sealed fluid communication with a nose bridge bladder member 88 through a connecting tube member 90. As seen in FIG. 6, in the illustrated embodiment, headgear bladder member 86 is positioned beneath or within rear portion 82 headgear component 76 and connecting tube member 90 is positioned beneath or within upper strap 78 of headgear component 76. For example, headgear bladder member 86 and connecting tube member 90 may be stitched, glued or otherwise adhered to the underside of rear portion 82 and upper strap 78. Alternatively, headgear bladder member 86 and connecting tube member 90 may simply rest beneath rear portion 82 and upper strap 78, held in place by the strapping forces of headgear component 76. In addition, as seen in FIG. 6, nose bridge bladder member 88 is positioned between the bottom end of connecting member 74 and the apex region 75 of faceplate portion 70 (in engagement therewith) at a point that is adjacent the pivot point of connecting member 74 (i.e., adjacent the nose bridge of patient 1). In this embodiment, bladder assembly 84 is not in fluid communication with cushion member 68.

In the illustrated embodiment, bladder assembly 84 is a unitary member wherein headgear bladder member 86, nose bridge bladder member 88 and connecting tube member 90 are formed as a unitary structure, for example using a molding technique. Alternatively, headgear bladder member 86, nose bridge bladder member 88 and connecting tube member 90 may be formed as separate components that are joined to one another in a fluid tight manner Bladder assembly 84 is made from a flexible, non-porous material, such as, without limitation, a rubber material, a polymer (e.g., silicone), or a sealed fabric, and is filled with a fluid medium. The fluid medium may be a gas, such as, without limitation, air, a liquid, such as, without limitation, water, a saline solution, or mineral oil, another suitable material that is able to flow, such as a gel, or any combination of such fluids. The fluid medium is free to flow within bladder assembly 84, i.e., back and forth between headgear bladder member 86 and nose bridge bladder member 88 through connecting tube member 90, thereby making bladder assembly 84 a resilient member.

The effect of the arrangement just described is that, as nose bridge bladder member 88 is inflated/deflated (as a result of fluid movement within bladder assembly 84) according to the pressure applied to headgear bladder member 86 by adjustment of headgear component 76 (primarily adjustment of upper straps 78), cushion member 68 rotate relative to the pivot point of connecting member 74. This rotation causes the apex region of cushion member 68 to move with respect to the nose bridge of patient 1, moving closer as the pressure on headgear bladder member 86 increases (i.e., as headgear component 76 is tightened) and moving away as the pressure on headgear bladder member 86 decreases (i.e., as headgear component 76 is loosened). Thus, tightening of headgear component 76 (primarily tightening of upper straps 78) compresses headgear bladder member 86 and pushes the fluid medium to nose bridge bladder 88, thereby tightening the fit of cushion member 68 against the nose of patient 1, and loosening of headgear component 76 (primarily loosening of upper straps 78) decompresses headgear bladder member 86 and pushes the fluid medium away from nose bridge bladder 88, thereby loosening the fit of cushion member 68 against the nose of patient 1.

Figure 7:
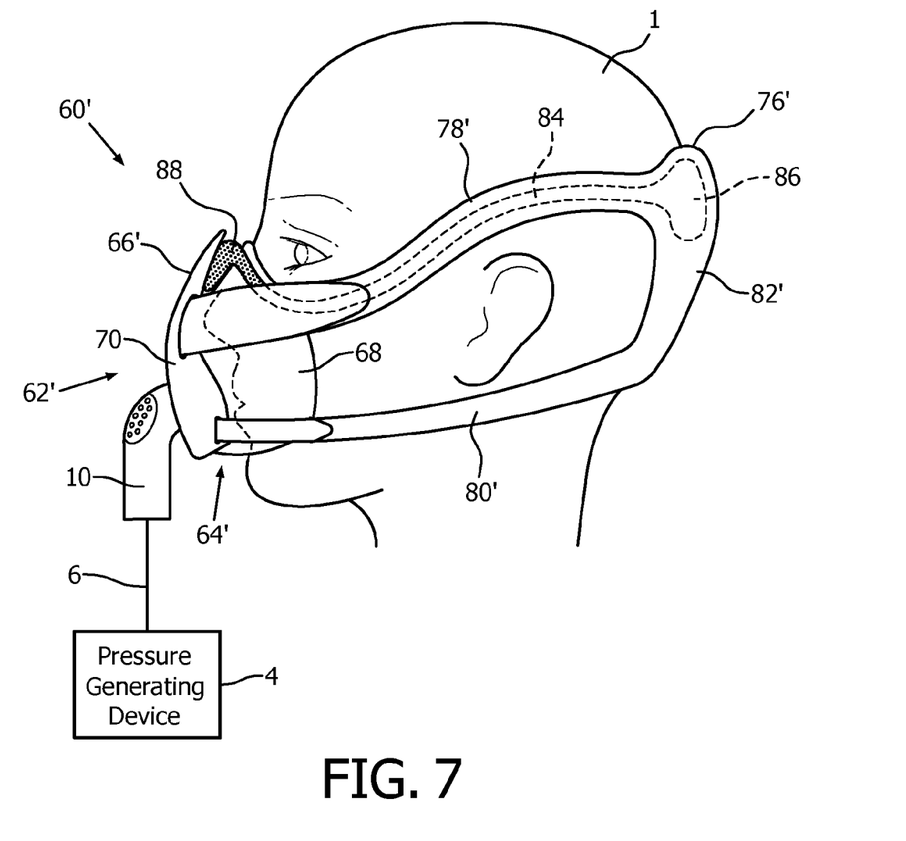

A system 60' adapted to provide a regimen of respiratory therapy to a patient according to still a further exemplary embodiment is generally shown in FIG. 7. System 60' includes a number of the same components as system 60, and like parts are labeled with like reference numerals. System 60' includes an alternative patient interface device 62' that includes an alternative patient sealing assembly 64'. As seen in FIG. 7, patient sealing assembly 64' includes alternative frame member 66' having cushion member 68 coupled thereto. Frame member 66' differs from frame member 66 in that it only includes faceplate portion 70 and does not include forehead support member 72 and connecting member 74. In addition, patient interface device 62' includes an alternative headgear component 76' having upper straps 78', lower straps 80', and rear portion 82', wherein upper straps 78' are curved and are attached to faceplate portion 70. In addition, patient interface device 62' includes a bladder assembly 84 as described herein that is provided beneath headgear component 76'.

Operation of patient interface device 62' is similar to operation of patient interface device 62. In particular, as nose bridge bladder member 88 is inflated/deflated (as a result of fluid movement within bladder assembly 84) according to the pressure applied to headgear bladder member 86 by adjustment of headgear component 76' (primarily adjustment of upper straps 78'), cushion member 68 rotate relative to apex of faceplate portion 70. This rotation causes the apex region of cushion member 68 to move with respect to the nose bridge of patient 1, moving closer as the pressure on headgear bladder member 86 increases (i.e., as headgear component 76' is tightened) and moving away as the pressure on headgear bladder member 86 decreases (i.e., as headgear component 76' is loosened). Thus, tightening of headgear component 76' (primarily tightening of upper straps 78') compresses headgear bladder member 86 and pushes the fluid medium to nose bridge bladder 88, thereby tightening the fit of cushion member 68 against the nose of patient 1, and loosening of headgear component 76' (primarily loosening of upper straps 78') decompresses headgear bladder member 86 and pushes the fluid medium away from nose bridge bladder 88, thereby loosening the fit of cushion member 68 against the nose of patient 1.

Figure 8:
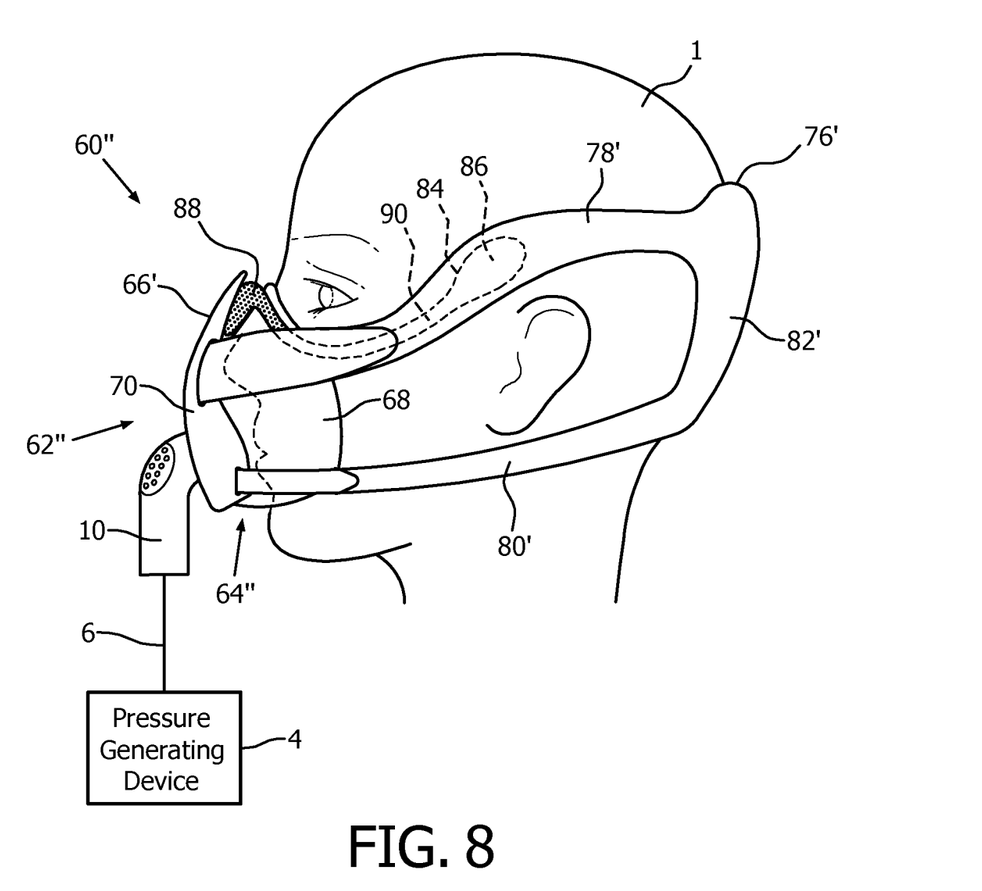

A system 60" adapted to provide a regimen of respiratory therapy to a patient according to another further exemplary embodiment is generally shown in FIG. 8. System 60" includes a number of the same components as system 60', and like parts are labeled with like reference numerals. System 60", however, includes a patient sealing assembly 64" having a patient interface device 62" wherein the bladder assembly 84 includes a shorter connecting tube member 90 such that headgear bladder member 86 is positioned beneath or within upper strap 78'. Operation of patient interface device 62" is similar to operation of patient interface device 62', in that tightening and loosening of headgear component 76' will inflate and deflate nose bridge bladder 88, thereby moving the apex region of cushion member 68.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
a patient sealing assembly including a cushion member;
a headgear assembly coupled to the patient sealing assembly, the headgear assembly including a strap; and
a bladder assembly comprising:
a headgear bladder member coupled to the strap,
a nose bridge bladder member positioned adjacent a top portion of the cushion, and
a connecting tube member provided between the headgear bladder member and the nose bridge bladder member, wherein the headgear bladder member is in sealed fluid communication with the nose bridge bladder member through the connecting tube member, the bladder assembly being filled with a fluid medium, wherein the bladder assembly is structured such that the nose bridge bladder member will be inflated as a pressure on the headgear bladder member increases in response to a force applied thereto by the strap increasing and such that the nose bridge bladder member will be deflated as the pressure on headgear bladder member decreases in response to the force applied thereto by the strap decreasing, and wherein inflation of the nose bridge bladder member causes the top of the cushion member to move in a first direction and deflation of the nose bridge bladder member causes the top of the cushion member to move in a second direction opposite the first direction.

2. The patient interface device according to claim 1, wherein the patient sealing assembly includes a frame member having a faceplate portion and a forehead support assembly including a connecting member and a forehead support member, the connecting member having a top end and a bottom end, the bottom end being coupled to a top of the faceplate portion, the forehead support member extending from the top end of the connecting member.

3. The patient interface device according to claim 2, wherein the headgear bladder member is positioned behind the forehead support member, the nose bridge bladder member is positioned adjacent the bottom end of the connecting member, and wherein inflation of the nose bridge bladder member causes the top of the cushion member to rotate relative to the bottom end of the connecting member in the first direction and deflation of the nose bridge bladder member causes the top of the cushion member to rotate relative to the bottom end of the connecting member in the second direction.

4. The patient interface device according to claim 2, wherein the bottom end of the connecting member is pivotably coupled to the top of the faceplate portion.

5. The patient interface device according to claim 2, wherein the connecting tube member extends along a rear surface of the connecting member.

6. The patient interface device according to claim 2, wherein the connecting tube member extends within a channel provided in the connecting member.

7. The patient interface device according to claim 2, wherein nose bridge bladder member is positioned between the bottom end of the connecting member and an outer surface of the top of the faceplate portion.

8. The patient interface device according to claim 1, wherein the patient sealing assembly includes a frame member having a faceplate portion, and wherein the nose bridge bladder member is positioned between an inner surface of the top of the faceplate portion and the top of the cushion member.

9. The patient interface device according to claim 8, wherein the top of the faceplate portion includes an orifice, and wherein the connecting tube member extends through the orifice.

10. The patient interface device according to claim 1, wherein the bladder assembly is not in fluid communication with the cushion member.

11. The patient interface device according to claim 1, wherein the nose bridge bladder member is part of the of the cushion member.

12. The patient interface device according to claim 10, wherein the top of the faceplate portion includes an orifice, and wherein the connecting tube member extends through the orifice.

13. The patient interface device according to claim 1, wherein the headgear assembly includes a rear portion coupled to the strap, and wherein the headgear bladder member is provided beneath or within the rear portion.

14. The patient interface device according to claim 1, wherein the headgear bladder member is provided beneath or within the strap.

15. A method of adjusting a patient interface device, comprising:
coupling the patient interface device to the patient's head, the patient interface device including a patient sealing assembly having a cushion member, and a bladder assembly having a headgear bladder member, a nose bridge bladder member, and a connecting tube member a provided between the headgear bladder member and the nose bridge bladder member, wherein the headgear bladder member is in sealed fluid communication with the nose bridge bladder member through the connecting tube member, the bladder assembly being filled with a fluid medium;
moving a top of the cushion member toward a nose bridge of the patient by inflating the nose bridge bladder member by increasing a pressure on the headgear bladder member; and
moving the top of the cushion member away from the nose bridge of the patient by deflating the nose bridge bladder member by decreasing the pressure on the headgear bladder member.

16. The method according to claim 15, wherein the patient sealing assembly includes a frame member having a faceplate portion the cushion member being coupled to the faceplate portion, wherein the patient interface device includes a forehead support assembly including a connecting member and a forehead support member, the connecting member having a top end and a bottom end, the bottom end being coupled to a top of the faceplate portion, the forehead support member extending from the top end of the connecting member, wherein the headgear bladder member is positioned behind the forehead support member and the nose bridge bladder member is positioned adjacent the bottom end of the connecting member.

17. The method according to claim 16, wherein nose bridge bladder member is positioned between the bottom end of the connecting member and an outer surface of the top of the faceplate portion.

18. The method according to claim 15, wherein the patient sealing assembly includes a frame member having a faceplate portion, and wherein the nose bridge bladder member is positioned between an inner surface of the top of the faceplate portion and the top of the cushion member.

19. The method according to claim 18, wherein the top of the faceplate portion includes an orifice, and wherein the connecting tube member extends through the orifice.

20. The method according to claim 15, wherein the bladder assembly is not in fluid communication with the cushion member.

21. The method according to claim 15, wherein the nose bridge bladder member is part of the of the cushion member.

22. The method according to claim 21, wherein the top of the faceplate portion includes an orifice, and wherein the connecting tube member extends through the orifice.

23. The method according to claim 15, wherein patient interface device includes a headgear assembly coupled to the patient sealing assembly, the headgear assembly including a strap, wherein the headgear bladder member is coupled to the strap, wherein the increasing the pressure on the headgear bladder member comprises increasing a force applied to the headgear bladder member by the strap and the decreasing the pressure on the headgear bladder member comprises decreasing the force applied to the headgear bladder member by the strap.

24. The method according to claim 23, wherein the headgear assembly includes a rear portion coupled to the strap, and wherein the headgear bladder member is provided beneath or within the rear portion.

25. The method according to claim 23, wherein the headgear bladder member is provided beneath or within the strap.

* * * * *